(12) United States Patent
Castro et al.

(10) Patent No.: US 8,680,300 B2
(45) Date of Patent: Mar. 25, 2014

(54) DIOXANES DERIVED FROM REGROUPING CARBOHYDRATES AND C-GLYCOSIDES, PROCESS FOR OBTAINING SAME AND USES THEREOF

(75) Inventors: Alicia Boto Castro, San Cristobal (ES); Rosendo Hernández González, San Cristobal (ES); Dácil Hernández Mesa, San Cristobal (ES); Eleuterio Álvarez González, Seville (ES); Raquel Marín Cruzado, La Laguna (ES); Mario Diaz González, La Laguna (ES)

(73) Assignees: Universidad de la Laguna, La Laguna (ES); Consejo Superior de Investigaciones Cientificas, Madrid (ES)

( * ) Notice: Subject to any disclaimer, the term of this patent is extended or adjusted under 35 U.S.C. 154(b) by 0 days.

(21) Appl. No.: 13/380,690

(22) PCT Filed: Jun. 25, 2010

(86) PCT No.: PCT/ES2010/070429
§ 371 (c)(1),
(2), (4) Date: Mar. 2, 2012

(87) PCT Pub. No.: WO2010/149817
PCT Pub. Date: Dec. 29, 2010

(65) Prior Publication Data
US 2012/0157520 A1    Jun. 21, 2012

(30) Foreign Application Priority Data
Jun. 25, 2009  (ES) .................................. 200930359

(51) Int. Cl.
*C07D 319/12* (2006.01)
*C07D 493/04* (2006.01)
*A61K 31/357* (2006.01)

(52) U.S. Cl.
USPC ........................... 549/364; 549/379; 514/452

(58) Field of Classification Search
USPC .................................. 549/364, 379; 514/452
See application file for complete search history.

(56) References Cited

U.S. PATENT DOCUMENTS

2003/0187027 A1    10/2003 Schreiber et al.

OTHER PUBLICATIONS

Boto, A. Y col. One-pot synthesis of acyclic nucleosides from carbohidrate derivatives, by combination of tandem and sequential reactions. The Journal of Organic Chemistry. 2007, vol. 72, N° 25, pp. 9523-9532.
Boto, A. Y col. Beta-Fragmentation of Primary Alkoxyl Radicals versus Hydrogen Abstraction: Synthesis of Polyols and alfa,omega-Differently Substituted Cyclic Ethers from Carbohydrates. The Journal of Organic Chemistry. 2003, vol. 68, N° 13, pp. 5310-5319. Todo el documento.
Boto, A. Y col. Coupling Radical and Ionic Processes: An Unusual Rearrangement Affords Sugar and C-Glycoside Derivatives. European Journal of Organic Chemistry. Aug. 2009, vol. 2009, N° 23, pp. 3853-3857.

*Primary Examiner* — Bernard Dentz
(74) *Attorney, Agent, or Firm* — Blank Rome LLP

(57) ABSTRACT

The present invention relates to compounds with a dioxane nucleus derived from carbohydrates and C-glucosides, process for obtaining same, to the use of such compounds as cytotoxic and antiproliferative agents and to the use thereof for producing a cancer treatment drug.

15 Claims, 6 Drawing Sheets

DIOXANES DERIVED FROM REGROUPING CARBOHYDRATES AND C-GLYCOSIDES, PROCESS FOR OBTAINING SAME AND USES THEREOF

This application is a national stage of International Application No. PCT/ES2010/070429, filed Jun. 25, 2010, which claims the benefit of Spanish Patent Application No. P 200930359, filed Jun. 25, 2009.

OBJECT OF THE INVENTION

The present invention relates to compounds with a dioxane nucleus derived from carbohydrates and C-glucosides, process for obtaining same, to the use of such compounds as cytotoxic and antiproliferative agents and to the use thereof for producing a cancer treatment drug.

PRIOR ART

The development of domino and sequential processes is a field of great interest to Sustainable Chemistry (or Green Chemistry). Said processes reduce synthesis time, on carrying out several reactions consecutively, without need for adding different substrates to the original substrates or extracting intermediate products from the reaction, thereby saving on materials and reducing the amount of residue to be treated. Application of these processes to the preparation of high added value products based on relatively inexpensive substrates is of special interest.

Domino and sequential processes that couple radical reactions and ionic reactions are known in the state of the art, occurring under mild conditions compatible with most of the functional groups (A. Boto, D. Hernández, R. Hernández, E. Álvarez, *J. Org. Chem.* 2007, 72, 9523-9532 and A. Boto, D. Hernández, R. Hernández, E. Suárez, *J. Org. Chem.* 2003, 68, 5310-5319). These processes are useful for splitting off anomeric O-radicals from carbohydrates or primary O-radicals.

As regards alternative methods for forming highly functionalised dioxanes, 1,2-diacetal-protected sugars have been described (S. V. Ley, A. Polara, *J. Org. Chem.* 2007, 72, 5943-5959). However, this method does not imply the direct transformation of the sugar ring into its dioxane analogue, but rather the creation of an additional ring. Additionally, said method only describes the formation of dioxanes for protecting sugar groups while performing different synthetic transformations, at the end of which the dioxane is destroyed.

DESCRIPTION OF THE INVENTION

The present invention provides a series of carbohydrate and C-glycoside analogues and a method for obtaining these by means of a domino chemical process, i.e. a process wherein several consecutive reactions are produced, without changing the reaction conditions and without need to isolate the intermediate products.

In a first aspect, the present invention discloses a compound with the formula (I):

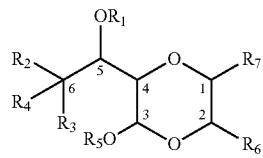

Formula (I)

or an isomer, salt, or solvate thereof, wherein
$R_1$ is selected from hydrogen, alkyl, acyl, aryl and heteroaryl;
$R_2$ is selected from hydrogen, alkyl and aryl;
$R_3$ is selected from hydrogen, alkyl and aryl;
$R_4$ is selected from hydrogen, alkyl, aryl, alkoxy, acyloxy, amine and amide; or $R_4$ and $R_5$ do not exist and an ether group is formed between the carbon in position 6 and the oxygen joined to the carbon in position 3;
$R_5$ is selected from hydrogen, alkyl and acyl;
$R_6$ is selected from alkyl, aryl and alkoxy;
$R_7$ is selected from alkoxy, alkyl, aryl, —$CH_2$—$COR_8$ and heterocycle;
$R_8$ is selected from alkyl and aryl.

The term "alkyl" refers, in the present invention, to aliphatic, linear or branched, saturated or unsaturated chains, preferably having 1 to 18 carbon atoms and, more preferably, 1 to 8 carbon atoms; for example, but not limited to, methyl, ethyl, n-propyl, i-propyl, n-butyl, tert-butyl, sec-butyl, n-pentyl, n-hexyl, n-heptyl, etc. The alkyl groups can optionally be substituted by one or more substituents such as halogen, hydroxyl, amine or carboxylic acid.

The term "acyl" relates, in the present invention, to a carboxylic acid by-product by elimination of a hydroxyl group. Carboxylic acid by-products have the general formula $R^4$—CO—, where $R^4$ is an alkyl group with the previous meanings and preferably relates to linear or branched alkyl groups ($C_1$-$C_{10}$); such as for example, but not limited to, propionyl, butanoyl, hexanoyl, pivaloyl, octanoyl and miristoyl.

The term "aryl" refers, in the present invention, to simple or multiple aromatic rings having between 5 and 18 bonds wherein a proton has been eliminated from the ring. Aryl groups are, for example, but not limited to, phenyl, nafthyl, diphenyl, indenyl, phenantryl and antracyl, and the aryl group preferably has between 5 and 10 carbon atoms. Aryl radicals can optionally be substituted for one or more substituents such as alkyl ($C_1$-$C_6$), halogen, hydroxyl or carboxylic acid.

The term "heteroaryl" refers, in the present invention, to an aryl radical, as defined previously, but where the ring has at least one heteroatom (oxygen, nitrogen, sulphur), such as for example, but not limited to, furyl, thiazolyl and radicals derived from pyrimidine and purine.

The term "alkoxy" refers, in the present invention, to an alkyl group joined to an oxygen atom, i.e. RO—, where R is an alkyl group, as defined previously.

The term "acyloxy" refers, in the present invention, to an acyl group [RC(O)] joined to an oxygen atom, i.e. RC(O)O—, where R is an alkyl or aryl group, as defined previously.

The term "amine" refers, in the present invention, to a radical with the formula $NH_2$, —NHR or —NRR', optionally quaternised, where R and R' are alkyl radicals, as defined previously.

The term "amide" refers, in the present invention, to a radical having the formula R—C(O)—NHR', where R and R' are alkyl radicals, as defined previously.

In a preferred embodiment, in the compound with the formula (I), $R_1$ is methyl.
In a preferred embodiment, in the compound with the formula (I), $R_2$ is hydrogen.
In a preferred embodiment, in the compound with the formula (I), $R_3$ is hydrogen.
In a preferred embodiment, in the compound with the formula (I), $R_4$ is acetoxy or alkoxy. Preferably, $R_4$ is acetoxy.
In a preferred embodiment, in the compound with the formula (I), $R_4$ and $R_5$ do not exist and an ether group is formed between the carbon in position 6 and the oxygen joined to the carbon in position 3, giving rise to a compound with the following general formula:

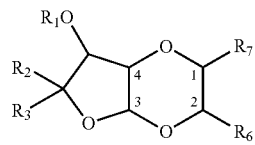

where $R_1$, $R_2$, $R_3$, $R_6$, $R_7$ have the previously described meaning.

In a preferred embodiment, in the compound with the formula (I), $R_6$ is O-methyl.

In a preferred embodiment, in the compound with the formula (I), $R_7$ is O-methyl.

In a preferred embodiment, in the compound with the formula (I), $R_7$ is —$CH_2$—$COR_8$ and $R_8$ is phenyl.

In another aspect, the present invention relates to a process for obtaining a compound with the formula (I), as described previously, which comprises a regioselective radical scission reaction of the $C_2$-$C_3$ bond with another oxidation reaction, followed by intramolecular cyclisation that generates a dioxane ring and, finally, the introduction of acyl or alkoxyl groups, in either an inter- or an intramolecular manner.

This process allows the conversion of easily obtainable sugars or glycosides to mono or bicyclical glycosides with a dioxane nucleus by re-grouping, wherein the furanose ring of the carbohydrate is split off and the resulting carbonyl group gives rise to intramolecular cyclisation that generates a dioxane ring. Given that the process of the present invention is a domino chemical process there is no need to isolate the intermediate products.

Domino processes have a significant advantage over conventional processes: on occurring several reactions consecutively and not having to purify the intermediate products, there is a significant savings in materials for reaction and purification, synthesis time and also a reduction in the residue to be processed. Therefore, these processes are of interest to chemical and pharmaceutical companies.

The process disclosed in the present invention has other significant advantages:
1) High added value products (possible drugs) can be obtained from sugar by-products that are easy to obtain.
2) Reactive agents with low toxicity are used (other radical scission processes use highly toxic metallic reactive agents, such as lead tetraacetate).
3) The reaction conditions are very mild and compatible with relatively labile substrates with many functional groups.
4) The process is simple. It occurs at ambient temperature, not being necessary to use reactors with cooling or heating systems, which cheapens synthesis.
5) The reactive agents are destroyed during aqueous extraction. Iodine gives iodides, diacetoxy iodobenzene gives iodosylbenzene, a by-product with relatively low toxicity and easy to treat.

In another aspect, the present invention relates to a compound with the formula (I), as previously described for use thereof as a drug.

In another aspect, the present invention relates to the use of a compound with the formula (I), as previously described for use as a cytotoxic or antiproliferative agent.

In another aspect, the present invention relates to the use of a compound with the formula (I), as previously described for producing a cancer treatment drug.

In another aspect, the present invention relates to a pharmaceutical composition comprising a compound with the formula (I), as previously described, and a pharmaceutically acceptable medium.

In a preferred embodiment, the present invention relates to a pharmaceutical composition, as previously described, which also comprises another active ingredient.

As used herein, the term "active ingredient" refers to any component that potentially provides a pharmacological activity or other different effect in the diagnosis, cure, mitigation, treatment or prevention of a disease or that affects the structure or function of human or animal bodies. The term includes those components that promote a chemical change in the preparation of the drug and are present therein in an envisaged modified manner that provides the specific activity or effect.

The compounds and compositions of this invention can be used on their own or together with other drugs to provide combined therapy. The other drugs can form part of the same composition or be provided as a separate composition for the simultaneous administration or separate administration thereof. The drugs to be combined with the compounds of the present invention can be drugs approved for treating any of the diseases or newly developed drugs.

Throughout the description and claims, the word "comprises" and variants thereof do not intend to exclude other technical characteristics, additives, components or steps. For persons skilled in the art, other objects, advantages and characteristics of the invention shall be partially inferred from the description and partially from the implementation of the invention. The following examples and drawings are provided by way of illustration and do not intend to be limiting of the present invention.

EXAMPLES

Figure 1:
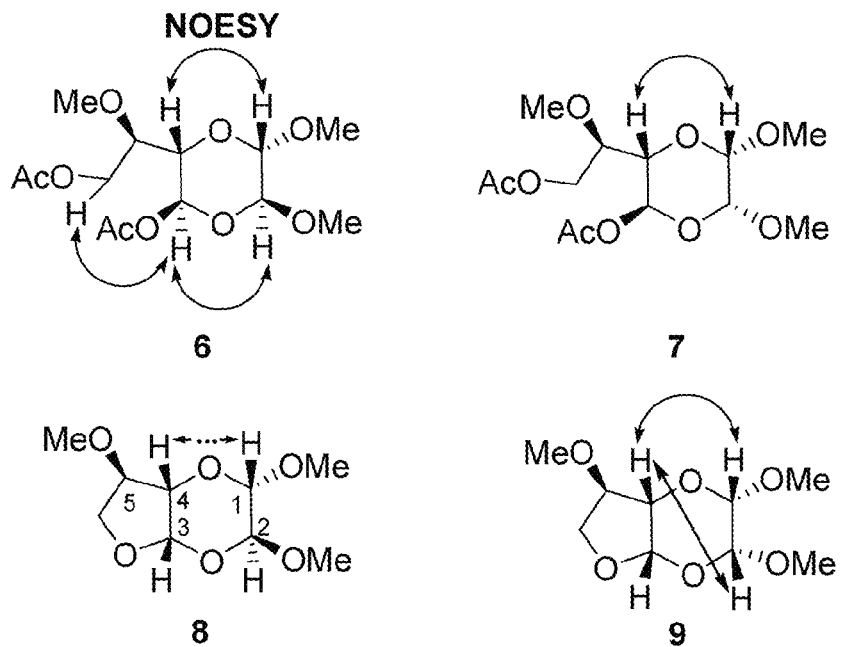
FIG. 1.—Shows NOESY experiments for products 6-9 (weak interaction is observed in 8).

The invention is illustrated below by means of trials conducted by the inventors, which highlights the specificity and effectiveness of the compounds with formula (I) and process for obtaining same.

1. Examples of Chemical Synthesis

Carbohydrates used as substrates were prepared using commercial D-galactopyranose 1 (Diagram 1). A silylation reaction was made using TBSCI, followed by methylation with NaH and MeI, forming galactofuranose 2. This synthetic intermediate was distilled, giving rise to diol 3. The primary hydroxyl group was protected by acetylation, generating compound 4, as well as the compound diacetylate 5.

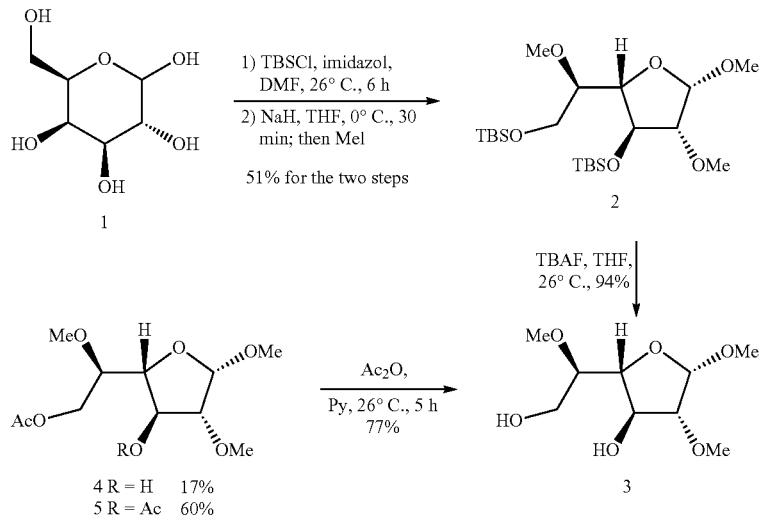

Diagram 1. Preparation of substrates derived from galactofuranose

When compound 5 (Diagram 2) was treated with (diacetoxy-iodo)benzene (DIB) and iodine in dichloromethane, under visible light irradiation, two products were obtained from a sequential scission-oxidation-cyclisation process. Structures 6 and 7 were assigned to these products. Additionally, when the substrate dihydroxylate 4 was subjected to the same reaction conditions, two fragmentation-oxidation-cyclisation products 8 and 9 were isolated.

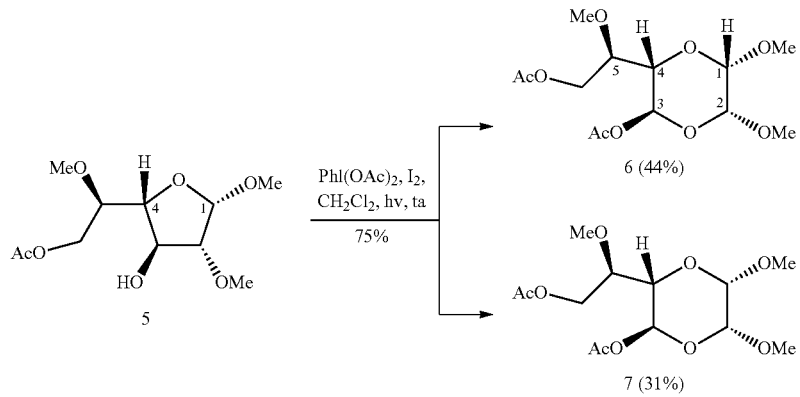

Diagram 2. Dioxanes derived from regrouping carbohydrates using scission-oxidation-cyclisation processes

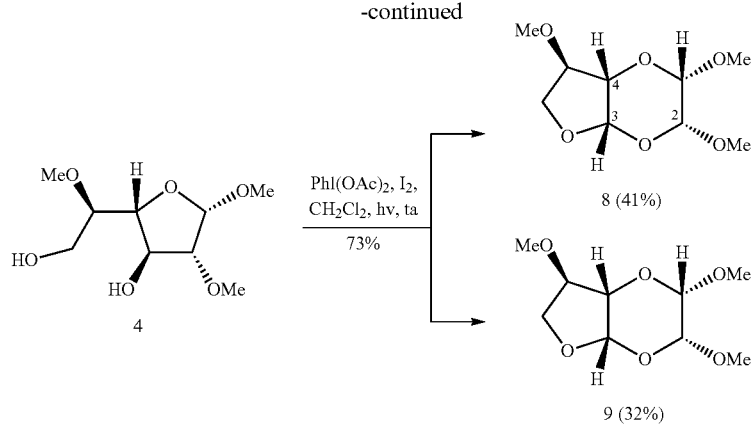

Figure 2:
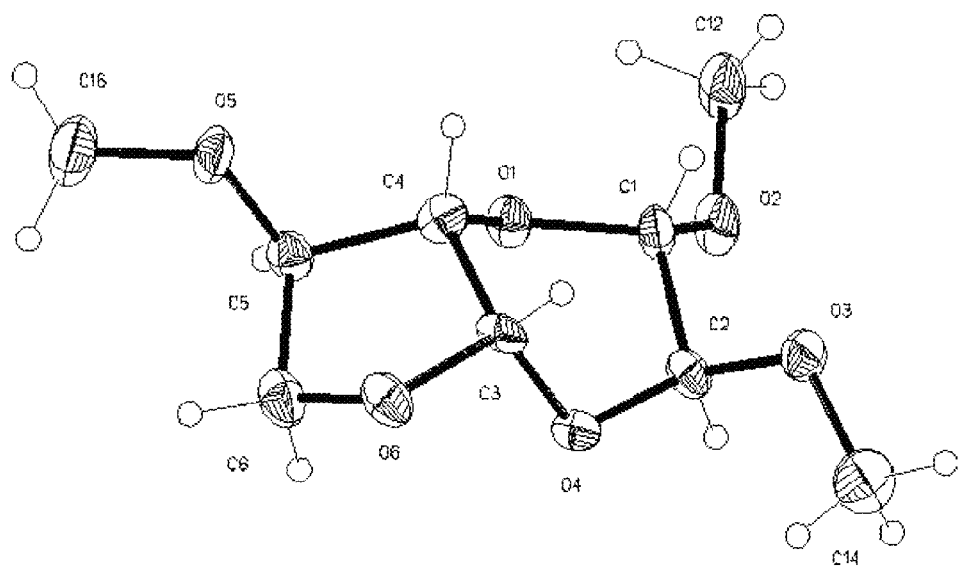
FIG. 2.—Shows ORTEP representation of compound 8 with thermal displacement ellipsoids drawn at the 50% probability level.

The stereochemistry of compounds 6-9 was determined in accordance with the experimental constants of $^1$H NMR (Table 1) and the NOESY experiments (FIG. 1). Additionally, the X-ray analysis of product 8 (FIG. 2) confirmed the proposed structure and configuration.

TABLE 1

Experimental coupling constants of RMN $^1$H.

| J (Hz) | Product 6 | Product 7 | Product 8 | Product 9 |
|---|---|---|---|---|
| $J_{1,2}$ | 4.3 | 1.6 | 3.7 | 1.4 |
| $J_{3,4}$ | 7.0 | 8.3 | 3.7 | 3.5 |
| $J_{4,5}$ | 3.0 | 3.0 | 2.1 | 1.5 |

These results can be explained in accordance with the mechanism shown in Diagram 3. Thus, the radical scission of substrates 4 or 5 generated a C-radical 10, which evolved due to oxidation into an oxycarbenium ion 11. The oxygen of the carbonyle group on C-3 acted as a nucleophile and the resulting ion was trapped either by acetate ions from the DIB (path [a]) or by the hydroxyl group on C-6 (path [b]). Path [a] generated the compounds 6 and 7, while path [b] gave rise to the bicyclical products 8 and 9. It must be pointed out that, during scission of the dihydroxylate substrate 4, the fragmentation of the secondary O-radical (that generated the compounds 8 and 9) is much faster than the scission of the primary radical (products of $C_5$-$C_6$ bond rupture were not detected).

Diagram 3. Possible mechanisims for regrouping carbohydrates using scission-oxidation-cyclisation processes.

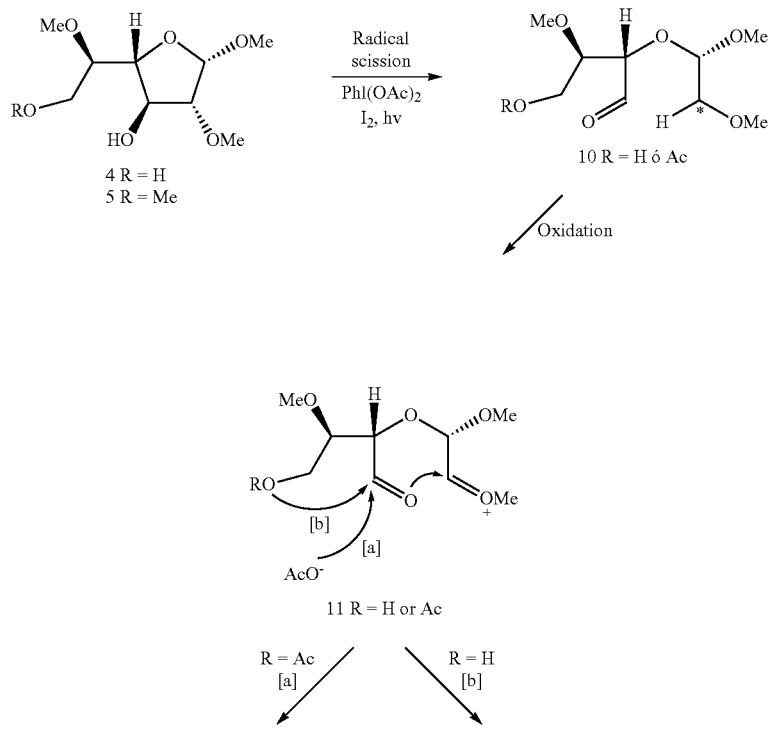

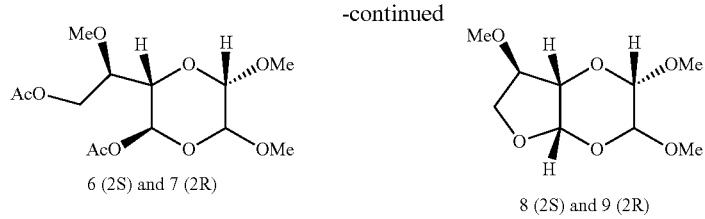

6 (2S) and 7 (2R)                    8 (2S) and 9 (2R)

Additionally, the formation of the by-products (2S) and (2R) in 1:1 ratio implies that rotation of the intermediates 10 or 11 around the $C_1$-$C_2$ bond is also fast.

Finally, the addition of acetate ions to C-3 (path [a]) took place on the side opposite the alkylic chain in C-4, giving rise to the products 3,4-trans 6 and 7. On the contrary, when the hydroxyl group on C-6 acted as a nucleophile (path [b]), the products 3,4-cis 8 and 9 were formed.

Products 6-9 are pyranose-type sugars. In order to determine whether this process was useful for preparing C-gycloside analogues, the 2-alkyl galactofuranose 14 (Diagram 4) was obtained from the diacetate 5 by alkylation of the anomeric position (giving rise to the phenone 12), followed by hydrolysis of the acetate groups (generating the alcohol 13). The substrate 13 was treated with DIB and iodine and irradiated using visible light. The scission-regrouping process efficiently generated the C-glycoside 14 analogue, the configuration of which was assigned as (1 R, 2S) (Table 2).

TABLE 2

Experimental and theoretical constants of RMN $^1$H for the possible isomers.

| J (Hz) | Product 14 | (1R, 2R) | (1R, 2S) | (1S, 2R) | (1S, 2S) |
|---|---|---|---|---|---|
| $J_{1,2}$ | 7.5 | 1.5 | 7.3 | 1.0 | 3.1 |
| $J_{3,4}$ | 2.8 | 3.0 | 2.6 | 3.4 | 2.8 |
| $J_{4,5}$ | 0.0 | 1.1 | 1.2 | 1.1 | 1.2 |

Diagram 4. Formation of C-glycoside analogues

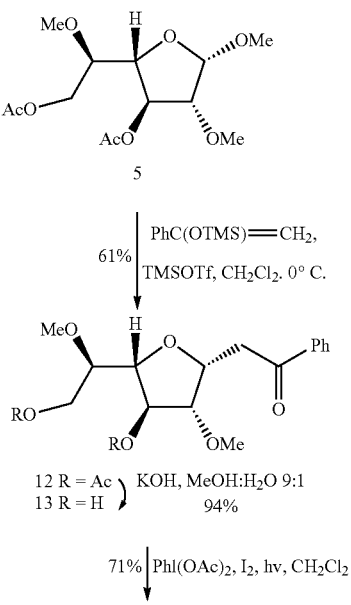

-continued

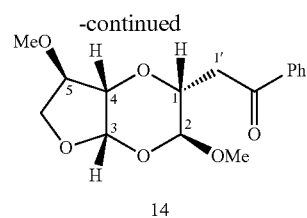

14

The formation of the product 14 must be highlighted, as unwanted secondary reactions did not occur (such as abstraction of the 1-H). Therefore, this methodology can be useful for preparing C-glycoside analogues.

General Procedure for the Scission-Oxidation-Cyclisation Process.

Iodine (25 mg, 0.1 mmol) and DIB (39 mg, 0.12 mmol) were added to an initial carbohydrate solution (0.1 mmol) in dry dichloromethane (2 mL). The resulting reaction was shaken for 2 h at 26° C., under visible light irradiation (using 80 W tungsten filament lamps purchased at hardware stores). The mixture was then poured over a 10% aqueous solution of sodium thyosulphate and extracted with dichloromethane. The organic phase was dried over sodium sulphate, filtered and the solvent eliminated under vacuum. The resulting residue was purified by silica gel column chromatography (eluents: ethyl hexane/acetate mixtures).

The compound 6 is a product with a rubbery consistency (44%). RMN $^1$H (500 MHz, CDCl$_3$): δ=2.09 (s, 3H), 2.12 (s, 3H), 3.45 (s, 3H), 3.46 (s, 3H), 3.51 (s, 3H), 3.52 (ddd, J=2.9, 5.8, 5.9 Hz, 1H, 5-H), 3.73 (dd, J=3.0, 7.0 Hz, 1H, 4-H), 4.28 (d, J=5.9 Hz, 2H, 6-H$_2$), 4.40 (d, J=4.3 Hz, 1H, 1-H), 4.51 (d, J=4.3 Hz, 1H, 2-H), 6.11 (d, J=7.0 Hz, 1H, 3-H) ppm. RMN $^{13}$C (125.7 MHz, CDCl$_3$): δ=20.8 (CH$_3$, Ac), 20.9 (CH$_3$, Ac), 56.3 (CH$_3$, OMe), 56.6 (CH$_3$, OMe), 59.4 (CH$_3$, OMe), 62.4 (CH$_2$, 6-C), 72.9 (CH, 4-C), 76.5 (CH, 5-C), 88.0 (CH, 3-C), 99.6 (CH, 2-C), 100.6 (CH, 1-C), 169.1 (C, CO), 170.7 (C, CO) ppm. EMAR (IE): calcd for $C_{12}H_{19}O_8$ [M$^+$ OMe] 291.1080; observing 291.1102.

The compound 7 is a product with a rubbery consistency (31%). RMN $^1$H (500 MHz, CDCl$_3$): δ=2.09 (s, 3H), 2.13 (s, 3H), 3.43 (s, 3H), 3.54 (s, 3H), 3.56 (m, 1H, 5-H), 3.57 (s, 3H), 3.74 (dd, J=3.0, 8.4 Hz, 1H, 4-H), 4.27 (dd, J=6.0, 11.5 Hz, 1H, 6-H$_a$), 4.31 (dd, J=6.0, 11.5 Hz, 1H, 6-H$_b$), 4.57 (d, J=1.7 Hz, 1H, 1-H), 4.62 (d, J=1.6 Hz, 1H, 2-H), 6.16 (d, J=8.3 Hz, 1H, 3-H) ppm. RMN $^{13}$C (125.7 MHz, CDCl$_3$): δ=20.9 (2×CH$_3$, Ac), 55.7 (CH$_3$, OMe), 57.1 (CH$_3$, OMe), 59.1 (CH$_3$, OMe), 62.2 (CH$_2$, 6-C), 75.5 (CH, 4-C), 76.3 (CH, 5-C), 84.7 (CH, 3-C), 97.3 (CH, 2-C), 99.0 (CH, 1-C), 168.7 (C, CO), 170.7 (C, CO) ppm. EMAR (IE): calcd for $C_{12}H_{19}O_8$ [M$^+$ OMe] 291.1080; observing 291.1081.

The product 8 was isolated as a crystalline solid (41%). P.f. 72-73° C. (crystallised with ethyl acetate/n-hexane). RMN $^1$H (500 MHz, CDCl$_3$): δ=3.40 (s, 3H), 3.50 (s, 3H), 3.53 (s, 3H), 3.93 (dd, J=1.7, 9.9 Hz, 1H, 6-H$_a$), 4.04 (ddd, J=1.9, 1.9, 4.9 Hz, 1H, 5-H), 4.10 (dd, J=2.1, 3.6 Hz, 1H, 4-H), 4.24 (d, J=3.7 Hz, 1H, 1-H), 4.29 (dd, J=4.9, 9.9 Hz, 1H, 6-H$_b$), 4.58 (d, J=3.7 Hz, 1H, 2-H), 5.39 (d, J=3.7 Hz, 1H, 3-H) ppm. $^{13}$C NMR (125.7 MHz, CDCl$_3$): δ=56.0 (CH$_3$, OMe), 56.5 (CH$_3$, OMe), 57.1 (CH$_3$, OMe), 70.9 (CH$_2$, 6-C), 77.7 (CH, 4-C), 83.9 (CH, 5-C), 95.3 (CH, 3-C), 97.9 (CH, 2-C), 98.2 (CH, 1-C) ppm. EMAR (IE): calcd for C$_8$H$_{13}$O$_5$ [M$^+$ OMe] 189.0763; observing 189.0753.

X-ray analysis of the product 8: C$_9$H$_{16}$O$_6$, M$_r$=220.22, colourless acicular crystal (0.50×0.21×0.06 mm$^3$) crystallised from ethyl acetate/n-hexane; monoclinic, spatial group C2 (no. 5), a=14.892(8) Å, b=4.395(2) Å, c=16.651(9) Å, V=1063.6(9) Å$^3$, Z=4, ρ$_{calcd}$=1.375 gcm$^{-3}$, F(000)=472, μ=0.116 mm$^{-1}$. 3841 reflections measured, of which 1251 were unique (R$_{int}$=0.0866). The asymmetrical unit of the structure was formed by a molecule of 8. Due to a high su in the Flack parameter, the Friedel pairs were averaged in the refinement (MERG 4 command). The absolute configuration of the new chiral centres was assigned considering other chiral centres of the molecule which were not affected by the process, the absolute configuration of which was known. A total of 139 refined parameters were obtained, with R$_1$=0.0588, for reflections where I>2σ(I), wR$_2$=0.1351 (complete data), GOF=1.019. Maximum/minimum residual electronic density: +0.263/−0.262 e.Å$^{-3}$.

The compound 9 is a product with a rubbery consistency (32%). RMN $^1$H (500 MHz, CDCl$_3$): δ=3.39 (s, 3H), 3.54 (s, 3H), 3.56 (s, 3H), 3.83 (d, J=9.6 Hz, 1H, 6-H$_a$), 4.00 (dd, J=1.0, 3.9 Hz, 1H, 5-H), 4.21 (dd, J=1.4, 3.1Hz, 1H, 4-H), 4.35 (dd, J=4.0, 9.6 Hz, 1H, 6-H$_b$), 4.48 (d, J=1.3 Hz, 1H, 1-H), 4.52 (d, J=1.4 Hz, 1H, 2-H), 5.27 (d, J=3.5 Hz, 1H, 3-H) ppm. RMN $^{13}$C (125.7 MHz, CDCl$_3$): δ=55.9 (CH$_3$, OMe), 56.8 (CH$_3$, OMe), 57.1 (CH$_3$, OMe), 70.1 (CH$_2$, 6-C), 77.0 (CH, 4-C), 84.4 (CH, 5-C), 94.6 (CH, 2-C), 96.6 (2×CH, 1-C+3-C) ppm. EMAR (IE): calcd for C$_8$H$_{13}$O$_5$ [M$^+$ OMe] 189.0763; observing 189.0770.

The compound 14 is a product with a rubbery consistency (71%). RMN $^1$H (500 MHz, CDCl$_3$): b=3.22 (d, J=7.5 Hz, 1'-H$_a$), 3.23 (d, J=4.5 Hz, 1'-H$_a$), 3.33 (s, 3H), 3.49 (s, 3H), 3.73 (d, J=4.1 Hz, 1H, 5-H), 3.84 (d, J=9.8 Hz, 1H, 6-H$_a$), 3.96 (ddd, J=4.5, 7.4, 7.5 Hz, 1H, 1-H), 4.08 (d, J=2.8 Hz, 1H, 4-H), 4.26 (dd, J=4.2, 9.7 Hz, 6-H$_a$), 4.70 (d, J=7.5 Hz, 1H, 2-H), 5.47 (d, J=2.8 Hz, 1H, 3-H), 7.47 (dd, J=7.6, 7.9 Hz, 2H, Ph), 7.58 (dd, J=7.4, 7.4 Hz, 1H, Ph), 7.95 (d, J=7.39 Hz, 2H, Ph) ppm. RMN $^1$H (500 MHz, C$_6$D$_6$): δ=2.76 (s, 3H), 2.95 (d, J=4.5 Hz, 1'-H$_a$), 2.96 (d, J=7.5 Hz, 1'-H$_b$), 3.26 (s, 3H), 3.44 (d, J=4.6 Hz, 1H, 5-H), 3.75 (d, J=9.6 Hz, 1H, 6-H$_a$), 3.80 (d, J=2.7 Hz, 4-H), 4.14 (dd, J=4.3, 9.6 Hz, 6-H$_a$), 4.20 (ddd, J=4.4, 7.4, 7.6 Hz, 1H, 1-H), 4.78 (d, J=7.5 Hz, 1H, 2-H), 5.58 (d, J=2.7 Hz, 1H, 3-H), 7.01 (dd, J=7.3, 7.8 Hz, 2H, Ph), 7.09 (dd, J=7.4, 7.4 Hz, 1H, Ph), 7.79 (d, J=7.1 Hz, 2H, Ph) ppm. RMN $^{13}$C (125.7 MHz, CDCl$_3$): δ=40.3 (CH$_2$, 1'-C), 56.3 (CH$_3$, OMe), 57.1 (CH$_3$, OMe), 71.0 (CH$_2$, 6-C), 72.0 (CH, 1-C), 76.2 (CH, 4-C), 83.9 (CH, 5-C), 98.0 (CH, 2-C), 98.8 (CH, 3-C), 128.2 (2×CH, Ph), 128.6 (2×CH, Ph), 133.3 (CH, Ph), 137.0 (C, Ph), 196.5 (C, CO) ppm. EMAR (IE): calcd for C$_{15}$H$_{17}$O$_6$ [M$^+$-OMe] 277.1076; observing 277.1053.

2. Biological Trials of Dioxanes 6-9 and 14

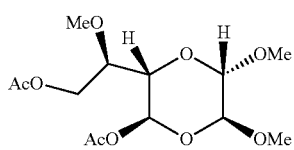

6

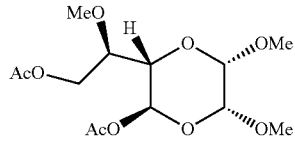

7

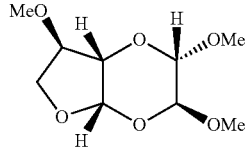

8

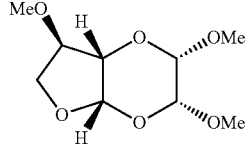

9

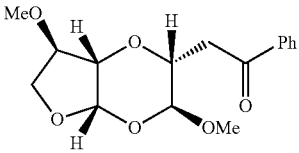

14

Methodology

Cell Culture Conditions and Treatments

Two stable cell lines of different origins were used for these trials: neural cell line HT22 from mouse hippocampus and line MCF7 from human breast cancer.

Both cell lines were grown in a DMEM culture medium supplemented with 10% foetal bovine serum and antibiotics at 37° C. with a 5% CO$_2$ atmosphere. 35-mm Petri dishes were used as growth media. When the cultures reached approximately 80% confluence they were exposed to the different compounds of the study for 24 hours at 37° C., at concentrations of 0.1, 1 and 5 μM. The compounds were previously diluted in DMSO.

Cytotoxicity and Cell Proliferation Trials

For the cytotoxicity trials, after 24 hours of treatment with the compounds, the cells were treated with trypsin, resuspending them in DMEM and counting them. On one hand, an aliquot of 100 μl was preserved for the total count of the cells present in Neubauer chambers. On the other, the rest of the cell volume (approximately 1 ml) was processed for dyeing with trypan blue to visualise those cells susceptible to dyeing (non-viable cells) against intact cells (viable cells). To this end, the ViCell (Beckman Coulter) quantifier was used.

Results

Visualisation of Cultures after Exposure to the Compounds

Figure 3:
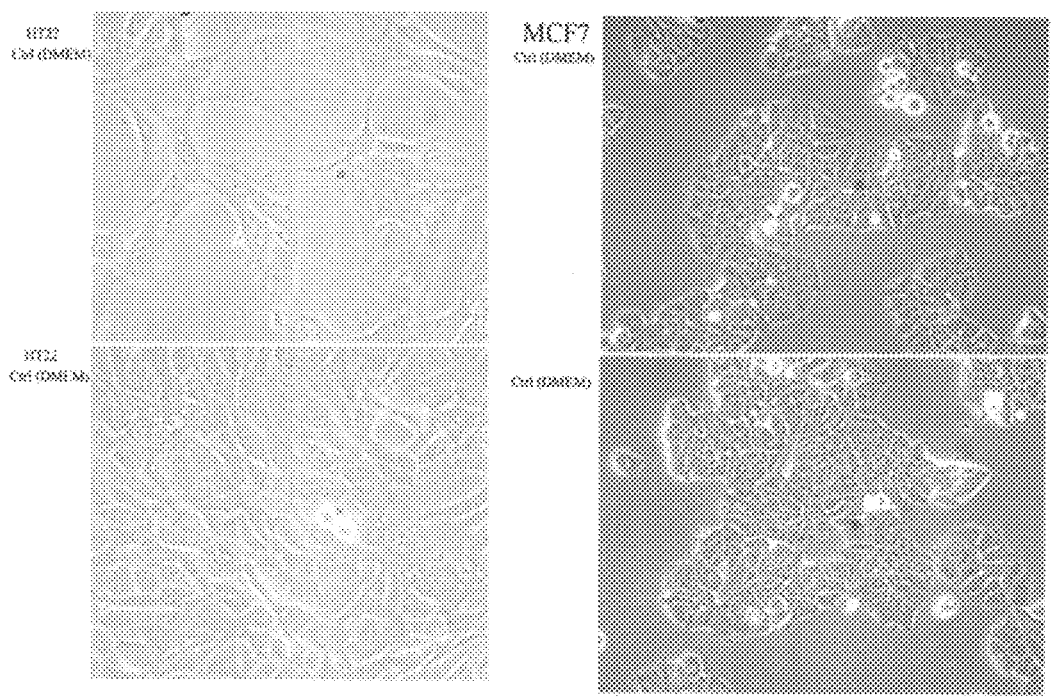
FIG. 3.—Shows images of the control cultures (not treated with the compounds) of cell line HT22 after 4 hours and of the control cultures of cell line MCF7 5 hours after starting the trials.
Figure 4:
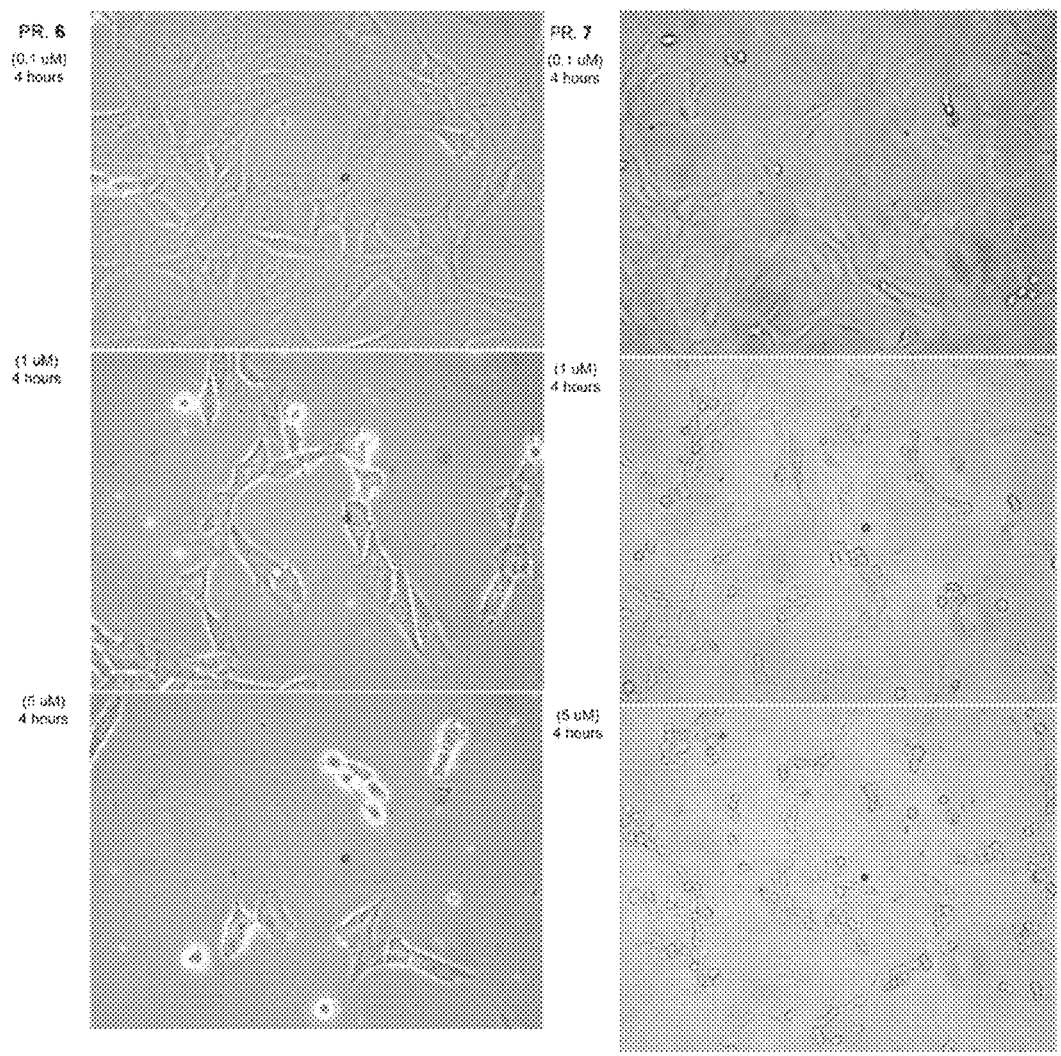
FIG. 4.—Shows images of the cultures of cell line HT22 after 4 hours of exposure to the indicated compounds and doses. A clear induction of cell death is observed at concentrations of 1 and 5 µM.
Figure 5:
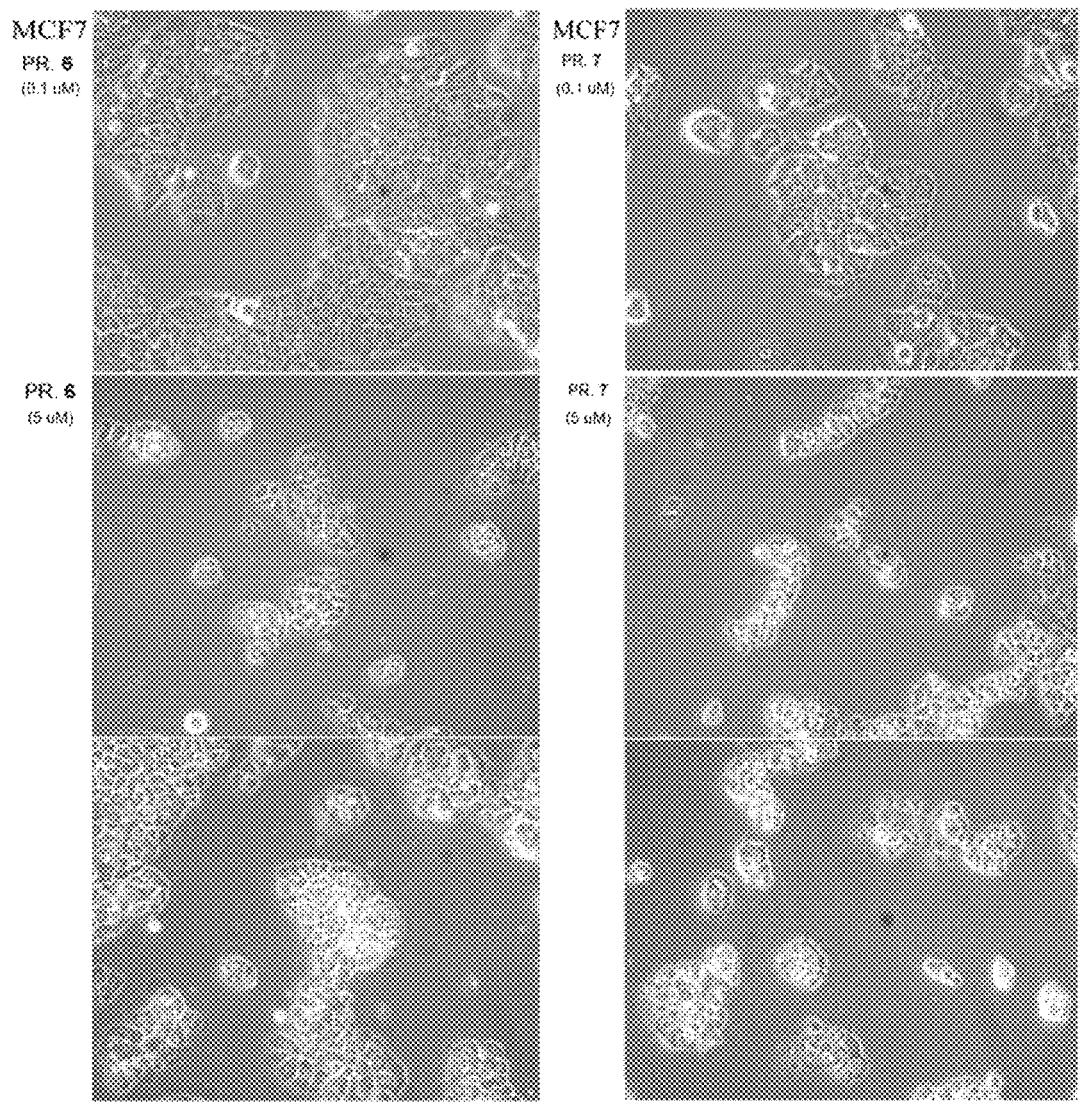
FIG. 5.—Shows images of the cultures of cell line MCF7 after five hours of exposure to the indicated compounds and doses. A clear induction of cell death (apoptosis) is observed at concentrations of 1 and 5 µM.

After 4-5 hours of treatment with the corresponding compounds, the cultures were visualised, observing a significant cytotoxic effect at doses of 5 μM of the open-chain compounds (6) and (7). (The control cultures of FIG. 3 were compared to the cultures of HT22 and MCF7 exposed to the compounds—FIGS. 4 and 5 respectively—).

Quantification of Toxicity and Cell Proliferation

Figure 6:
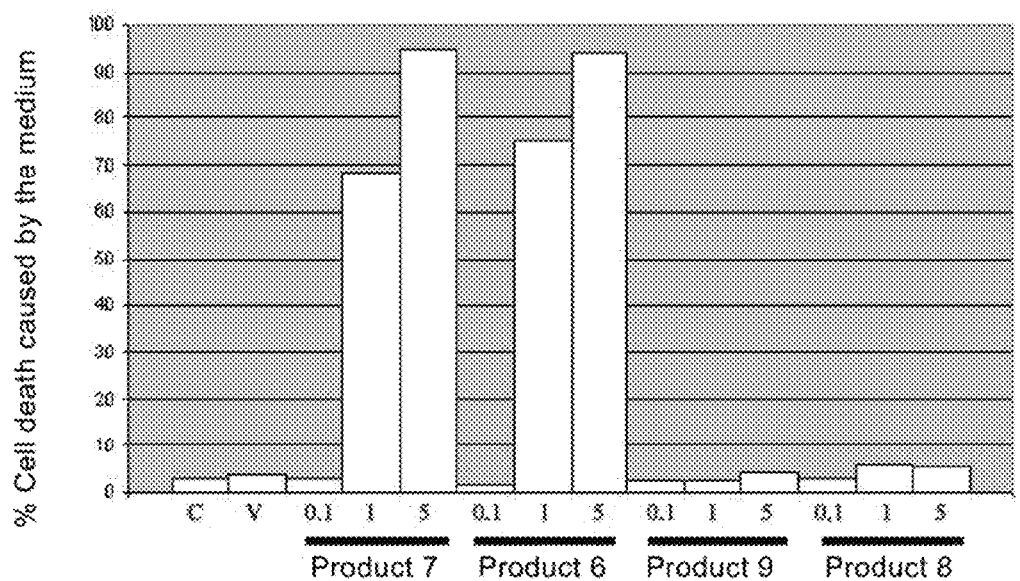
FIG. 6.—Shows the percentage of cell death caused by the different compounds, quantified using trypan blue dye in neural cell line HT22. The results were normalised in accordance with the mortality caused by the medium (V, DMSO at 0.01%). Three trials per experimental group were conducted.

In the case of line HT22, it was observed that the products 6 and 7 caused a toxicity of between 55-75% at doses of 1 μM, in comparison to the toxicity caused by the medium (DMSO at 0.01%, V in FIG. 6). This cytotoxic effect was increased more than 90% in the case of concentrations of 5 μM.

Figure 7:
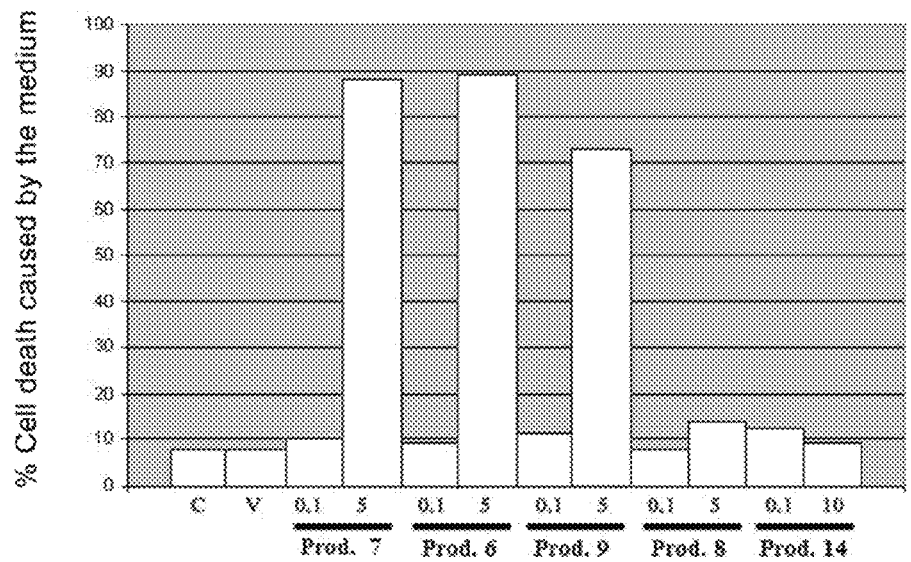
FIG. 7.—Shows the percentage of cell death caused by the different compounds, quantified using trypan blue dye in cell line MCF7. The results were normalised to the mortality caused by the medium (V, DMSO at 0.01%). Three trials were conducted per experimental group FIG. 8.—Shows the percentage of inhibition of the proliferation of the neurons in the presence of the indicated cyclical compounds with regard to the proliferation observed in the presence of the medium (V, DMSO at 0.01%). Three trials were conducted per experimental group.

In the case of MCF7 cells, similar high toxicity results were observed using compounds 6 and 7. High toxicity (>65%) was also observed in these cells using the cyclical compound 9 (FIG. 7).

Figure 8:
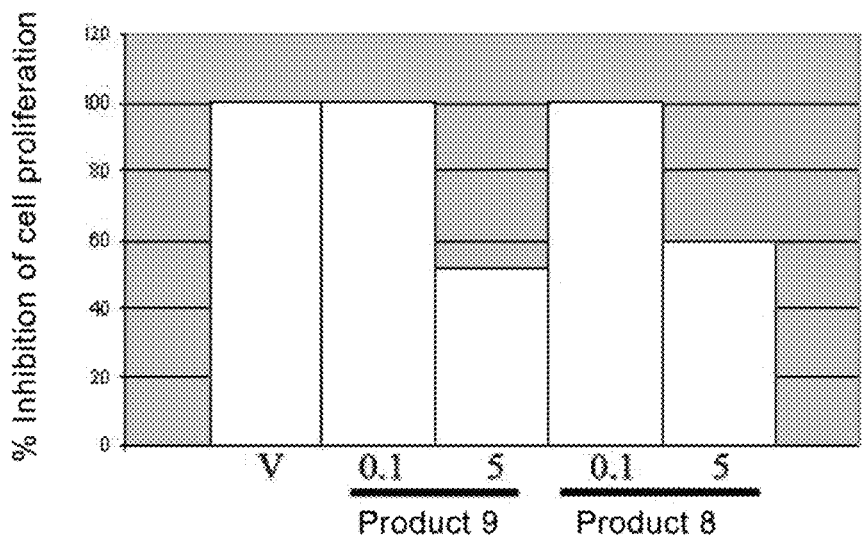
Figure 9:
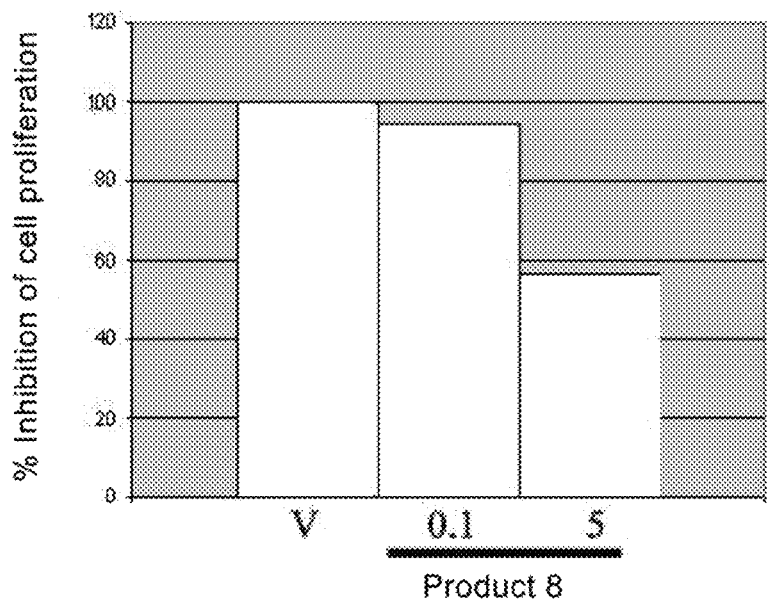
FIG. 9.—Shows the percentage of inhibition of the proliferation of cancer cells in the presence of product 8 with regard to the proliferation observed in the presence of the medium (V, DMSO at 0.01%). Three trials were conducted per experimental group.

Additionally, it must be highlighted that both bicyclical compounds (products 8 and 9) caused a decrease of approximately 50% in the normal proliferation of neural cell line HT22 (FIG. 8). These partial proliferation inhibition results were corroborated in the MCF7 breast cancer cells using compound 8 (FIG. 9).

CONCLUSION

From the data obtained it can be inferred that the open-chain compounds 6 and 7 are highly cytotoxic at concentrations of 1 and 5 μM both in neural cell line HT22 and in breast cancer line MCF7. In the case of the cyclical compounds, product 8 has antiproliferative effects in both cell types, while the cyclical compound 9 has antiproliferative effects in HT22 and high toxicity in MCF7.

The invention claimed is:

1. A compound having the formula (I):

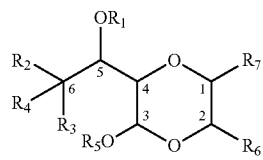

Formula (I)

or an isomer, salt, or solvate thereof, wherein $R_1$ is selected from hydrogen, alkyl, acyl, aryl and heteroaryl;

$R_2$ is selected from hydrogen, alkyl and aryl;

$R_3$ is selected from hydrogen, alkyl and aryl;

$R_4$ is selected from hydrogen, alkyl, aryl, alkoxy, acyloxy, amine and amide;

and $R_5$ is selected from hydrogen, alkyl and acyl; or $R_4$ and $R_5$ do not exist and an ether linkage is formed between the carbon atom in position 6 and the oxygen atom joined to the carbob atom in position 3;

$R_6$ is selected from alkyl, aryl and alkoxy;

$R_7$ is selected from alkoxy, alkyl, aryl, —$CH_2$—$COR_8$ and heterocycle;

$R_8$ is selected from alkyl and aryl.

2. The compound according to claim 1, wherein $R_1$ is methyl.

3. The compound according to claim 1, wherein $R_2$ and $R_3$ are hydrogen.

4. The compound according to claim 1, wherein $R_4$ is acetoxy or alkoxy.

5. The compound according to claim 1, wherein $R_5$ is acetyl.

6. The compound according to claim 1, wherein $R_4$ and $R_5$ do not exist and an ether linkage is formed between the carbon atom in position 6 and the oxygen joined to the carbon atom in position 3, giving rise to a compound having the following formula:

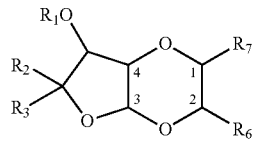

7. The compound according to claim 1, wherein $R_6$ is O-methyl.

8. The compound according to claim 1, wherein $R_7$ is O-methyl.

9. The compound according to claim 1, wherein $R_7$ is —$CH_2$—$COR_8$ and $R_8$ is phenyl.

10. A process for preparing a compound according to claim 1, comprising (a) a regioselective radical scission reaction of the $C_2$-$C_3$ bond with an oxidation reaction, (b) an intramolecular cyclisation to generate a dioxane ring and, (c) introduction of acyl or alkoxyl groups, in either an inter- or an intramolecular manner.

11. A cytotoxic or antiproliferative agent comprising the compound with the formula (I), according to claim 1.

12. A method of treating cancer in a patient in need thereof comprising administering an effective amount of a compound according to claim 1.

13. A pharmaceutical composition comprising a compound according to claim 1, and a pharmaceutically acceptable vehicle.

14. The pharmaceutical composition according to claim 13, further comprising another active ingredient.

15. The method according to claim 12, wherein the cancer is breast cancer.

* * * * *